(12) United States Patent
Toth et al.

(10) Patent No.: US 7,260,182 B2
(45) Date of Patent: *Aug. 21, 2007

(54) METHOD AND APPARATUS OF RADIOGRAPHIC IMAGING WITH AN ENERGY BEAM TAILORED FOR A SUBJECT TO BE SCANNED

(75) Inventors: Thomas L. Toth, Brookfield, WI (US); John Eric Tkaczyk, Delanson, NY (US); Jiang Hsieh, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/419,851

(22) Filed: May 23, 2006

(65) Prior Publication Data

US 2006/0198496 A1    Sep. 7, 2006

Related U.S. Application Data

(63) Continuation of application No. 10/605,789, filed on Oct. 27, 2003, now Pat. No. 7,076,029.

(51) Int. Cl.
*G21K 3/00* (2006.01)
*A61B 6/03* (2006.01)

(52) U.S. Cl. .................. 378/157; 378/16; 378/158; 378/159

(58) Field of Classification Search .......... 378/4, 378/16, 156, 157, 158, 159; 250/505.1
See application file for complete search history.

(56) References Cited

U.S. PATENT DOCUMENTS

| 3,717,768 | A | 2/1973 | Edholm et al. |
|---|---|---|---|
| 3,755,672 | A | 8/1973 | Edholm et al. |
| 4,181,858 | A | 1/1980 | Moore |
| 4,371,976 | A * | 2/1983 | Wagner ............... 378/16 |
| 4,998,268 | A | 3/1991 | Winter |
| 5,019,713 | A | 5/1991 | Schmidt |
| 5,287,396 | A * | 2/1994 | Stegehuis ............. 378/156 |
| 5,379,333 | A | 1/1995 | Toth |
| 5,400,378 | A | 3/1995 | Toth |
| 5,450,462 | A | 9/1995 | Toth et al. |
| 5,457,724 | A | 10/1995 | Toth |
| 5,970,112 | A | 10/1999 | Hsieh |
| 6,137,857 | A | 10/2000 | Hoffman et al. |
| 6,148,062 | A | 11/2000 | Romeas |

(Continued)

FOREIGN PATENT DOCUMENTS

JP    08266523 A    10/1996

*Primary Examiner*—Chih-Cheng G Kao
(74) *Attorney, Agent, or Firm*—Ziolkowski Patent Solutions Group, SC

(57) ABSTRACT

A method and apparatus for tailoring the profile of an x-ray beam for radiographic imaging for a specific subject is disclosed. The invention includes a filter assembly having a pair of filters, each of which may be dynamically controlled by a motor assembly during data acquisition. The filters are positionable in the x-ray beam so as to shape the intensity profile of the x-ray beam. In one exemplary embodiment, the filters are dynamically positioned during CT data acquisition based on the shape of the subject. A method of determining the shape of the subject prior to CT data acquisition is also disclosed.

12 Claims, 4 Drawing Sheets

U.S. PATENT DOCUMENTS

| | | |
|---|---|---|
| 6,173,039 B1 | 1/2001 | Hampel et al. |
| 6,269,501 B1 | 8/2001 | Li et al. |
| 6,307,918 B1 | 10/2001 | Toth et al. |
| 6,501,828 B1 | 12/2002 | Popescu |
| 6,775,352 B2 | 8/2004 | Toth et al. |
| 6,836,535 B2 | 12/2004 | Toth et al. |
| 6,934,354 B2 | 8/2005 | Hoffman |
| 6,954,516 B2 | 10/2005 | Li et al. |
| 6,968,030 B2 | 11/2005 | Hoffman |
| 7,031,434 B1 | 4/2006 | Saunders et al. |
| 7,046,756 B2 | 5/2006 | Hoffman |
| 7,076,029 B2 * | 7/2006 | Toth et al. .................. 378/158 |
| 2003/0195416 A1 | 10/2003 | Toth |
| 2003/0199757 A1 | 10/2003 | Toth et al. |
| 2004/0217291 A1 | 11/2004 | Hoge |

* cited by examiner

METHOD AND APPARATUS OF RADIOGRAPHIC IMAGING WITH AN ENERGY BEAM TAILORED FOR A SUBJECT TO BE SCANNED

CROSS REFERENCE TO RELATED APPLICATIONS

The present application is continuation of and claims priority of U.S. Ser. No. 10/605,789 filed Oct. 27, 2003 now U.S. Pat. No. 7,076,029, the disclosure of which is incorporated herein by reference.

BACKGROUND OF THE INVENTION

The present invention relates generally to diagnostic imaging and, more particularly, to a method and apparatus of dynamically filtering radiation emitted toward a subject during radiographic imaging in a manner tailored to the shape and/or position of a subject to be imaged.

Typically, in radiographic imaging systems, an x-ray source emits x-rays toward a subject or object, such as a patient or a piece of luggage. Hereinafter, the terms "subject" and "object" may be interchangeably used to describe anything capable of being imaged. The beam, after being attenuated by the subject, impinges upon an array of radiation detectors. The intensity of the attenuated beam radiation received at the detector array is typically dependent upon the attenuation of the x-rays. Each detector element of the detector array produces a separate electrical signal indicative of the attenuated beam received by each detector element. The electrical signals are transmitted to a data processing system for analysis which ultimately produces an image.

In computed tomography (CT) imaging systems, the x-ray source and the detector array are rotated about a gantry within an imaging plane and around the subject. X-ray sources typically include x-ray tubes, which emit the x-rays as a beam at a focal point. X-ray detectors typically include a collimator for collimating x-ray beams received at the detector, a scintillator for converting x-rays to light energy adjacent the collimator, and a photodiode for receiving the light energy from an adjacent scintillator and producing electrical signals therefrom. Typically, each scintillator of a scintillator array converts x-rays to light energy. Each photodiode detects the light energy and generates a corresponding electrical signal. The outputs of the photodiodes are then transmitted to the data processing system for image reconstruction.

There is increasingly a need to reduce radiation dosage received by a patient during an imaging session. It is generally well known that significant dose reduction may be achieved by using a "bowtie" filter to shape the intensity profile of an x-ray beam. Surface dose reductions may be as much as 50% using a bowtie filter. It is also generally known that different anatomical regions of a patient may advantageously mandate different shaped bowtie filters to reduce radiation dosage. For example, scanning of the head or a small region of a patient may require a bowtie filter shaped differently than a filter used during a large body scanning session. It is therefore desirable to have an imaging system with a large number of bowtie filter shapes available to best fit each patient. However, fashioning an imaging system with a sufficient number of bowtie filters to accommodate the idiosyncrasies encountered during scanning of numerous patients can be problematic in that each individual patient cannot be contemplated. Additionally, manufacturing an imaging system with a multitude of bowtie filters increases the overall manufacturing cost of the imaging system.

Further, for optimum dose efficiency, i.e. best image quality at the lowest possible dose, the attenuation profile created by the bowtie filter should be particular to the patient. That is, it is desirable and preferred that when selecting a pre-patient filter that the patient's size, shape, and relative position be taken into account. By taking the patient's size, shape, and position into consideration, radiation exposure can be tailored to the specific patient. Further, it is generally well-known that photon counting (PT) and energy discriminating (ED) CT systems are not possible today, primarily because the large dynamic range of photon flux rates exceeds the count rate capabilities of current PT and ED detectors. Tailoring the pre-patient filter to the subject to be scanned also allows for conforming the filter to minimize photon flux rates in a range suitable to permit continued development of PT and ED CT systems. As noted above, the differences in patients in the potential subject pool are significantly large and fitting a CT system with a pre-patient filter for each possible patient profile is more than cost prohibitive; its simply not practical.

Therefore, it would be desirable to design an apparatus and method of dynamically filtering the radiation emitted toward the subject for data acquisition in a manner tailored to particular physical characteristics of the subject. It would be further desirable to have a system that tailors the radiation emitted toward the subject during data acquisition based on a scout scan of the subject.

BRIEF DESCRIPTION OF THE INVENTION

The present invention is a directed method and apparatus for defining a tailored attenuation profile of a pre-subject, beam shaping filter that overcomes the aforementioned drawbacks. A filter assembly is provided and has a pair of filters, each of which is dynamically controllable by a motor assembly during data acquisition. The filters may be positioned in the x-ray beam so as to shape the profile of the x-ray beam. In one exemplary embodiment, the filters are dynamically positioned during CT data acquisition based on the shape of the subject. A method of determining the shape of the subject prior to CT data acquisition is also disclosed.

Therefore, in accordance with one aspect of the present invention, a beam shaping filter assembly is provided. The filter assembly includes a first moveable filter having a non-uniform thickness and a second moveable filter independent of the first moveable filter and having a non-uniform thickness. Each filter is configured to be placed in a high frequency electromagnetic energy beam for attenuation of the beam for radiographic data acquisition.

In accordance with another aspect, a CT system is disclosed that includes a rotatable gantry having an opening to receive a subject to be scanned and a high frequency electromagnetic energy projection source configured to project a high frequency electromagnetic energy beam toward the subject. A pre-subject filter assembly including a pair of filters and a scintillator array having a plurality of scintillator cells wherein each cell is configured to detect high frequency electromagnetic energy passing through the subject are also provided. The CT system also includes a photodiode array optically coupled to the scintillator array and comprising a plurality of photodiodes configured to detect light output from a corresponding scintillator cell and a data acquisition system (DAS) connected to the photodiode array and configured to receive the photodiode outputs. An image reconstructor is provided and connected to the DAS and configured to reconstruct an image of the subject from the photodiode outputs received by the DAS. The CT system further includes a controller configured to independently position each filter of the pair of filters in the high frequency electromagnetic energy beam so as to modulate the beam to have a profile that substantially matches at least an approximate shape of the subject.

According to another aspect, the present invention includes an x-ray filter assembly having a first filter and a second filter. A first motor assembly is connected to the first filter and a second motor assembly is connected to the second filter. The first and the second motor assemblies are configured to independently position a respective filter in an x-ray path to define an attenuation profile that substantially approximates a target shape.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

Figure 1:
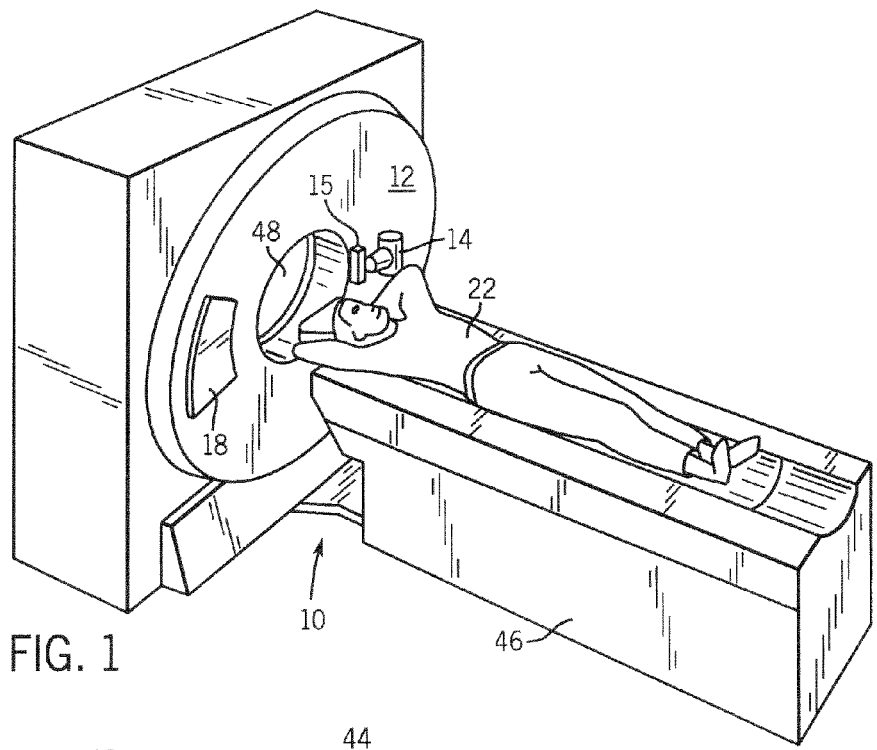
FIG. 1 is a pictorial view of a CT imaging system.
Figure 2:
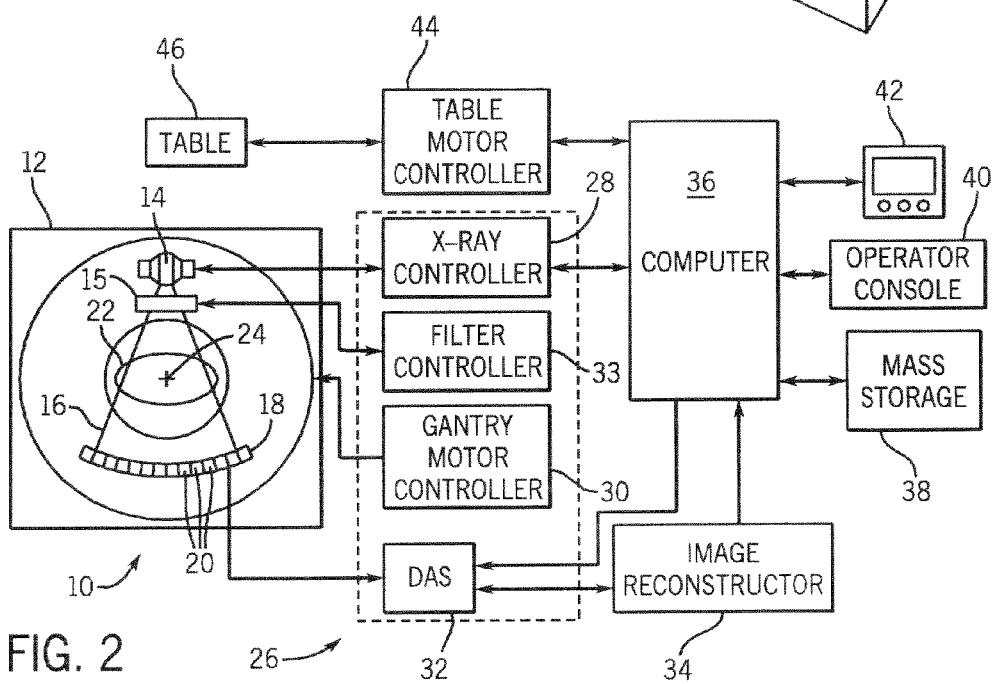
FIG. 2 is a block schematic diagram of the system illustrated in FIG. 1.
Figure 3:
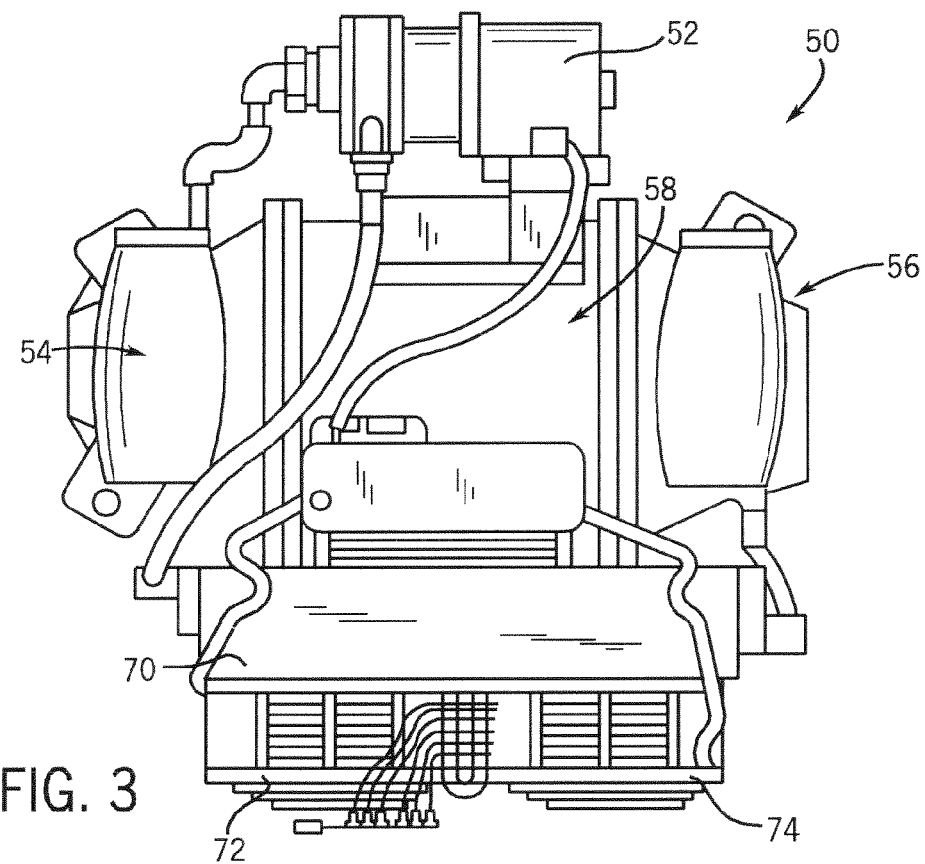
FIG. 3 is a plan view of a representative x-ray system.
Figure 4:
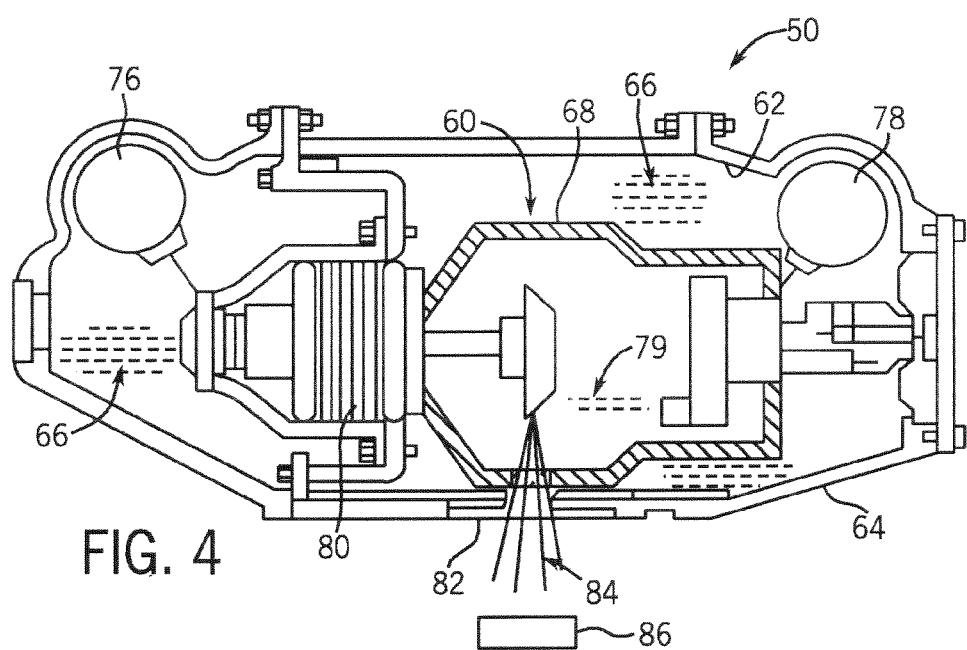
FIG. 4 is a sectional view of a portion of the x-ray system shown in FIG. 1.
Figure 8:
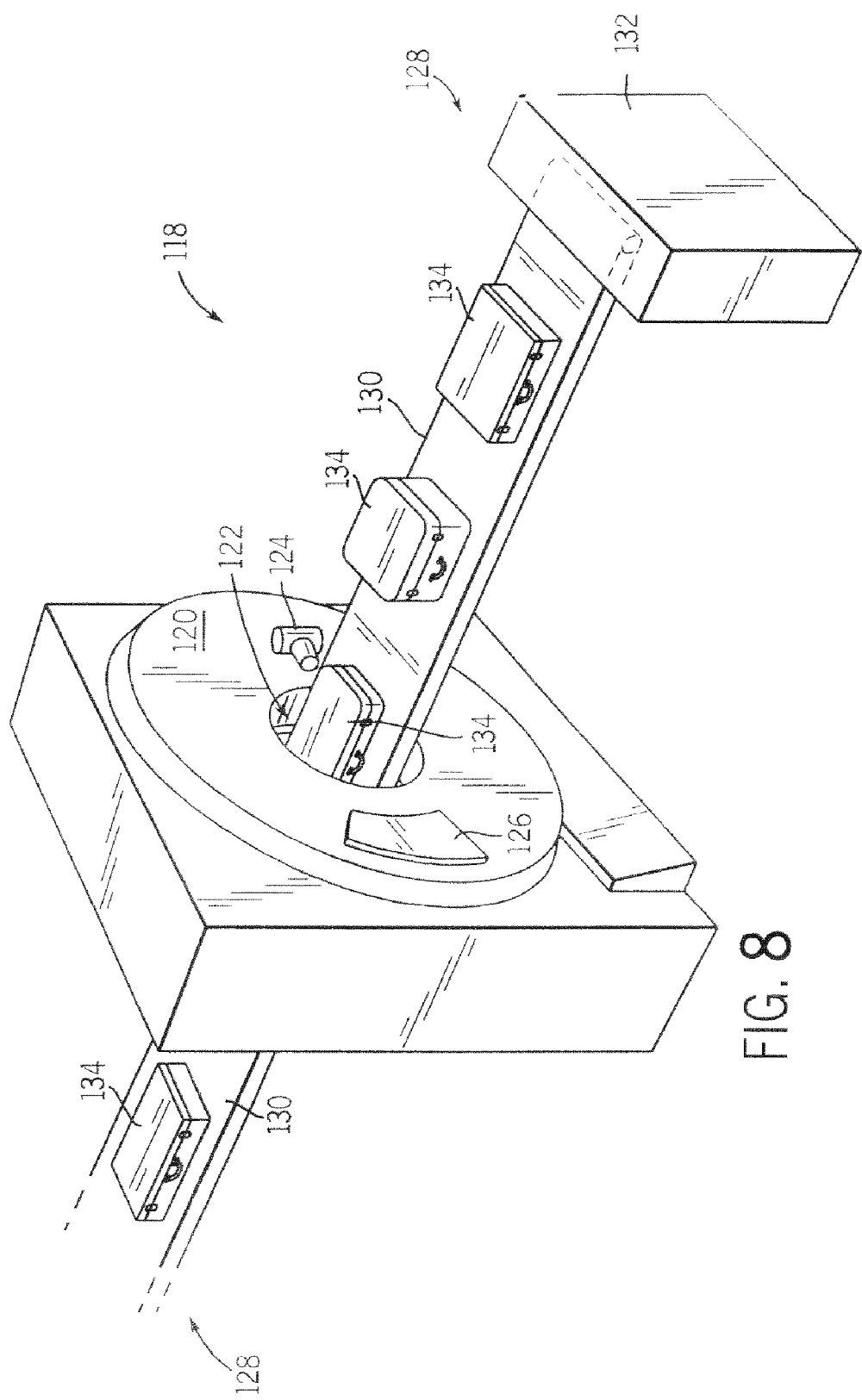
FIG. 8 is a pictorial view of a CT system for use with a non-invasive package inspection system.

The present invention is described with respect to a radiographic imaging system such as the CT system shown in FIGS. 1-2 and 8 and the x-ray system shown in FIGS. 3-4. However, it will be appreciated by those skilled in the art that the present invention is equally applicable for use with other radiographic imaging systems. Moreover, the present invention will be described with respect to the emission and detection of x-rays. However, one skilled in the art will further appreciate, that the present invention is equally applicable for the emission and detection of other high frequency electromagnetic energy.

Referring to FIGS. 1 and 2, a "third generation" CT imaging system 10 is shown as including a gantry 12. The present invention, however, is applicable with other CT systems. Gantry 12 has an x-ray source 14 that projects a beam of x-rays 16 through filter assembly 15 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14, a gantry motor controller 30 that controls the rotational speed and position of gantry 12, and filter assembly controller 33 that controls filter assembly 15. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 which controls a motorized table 46 to position patient 22 and gantry 12. Particularly, table 46 moves portions of patient 22 through a gantry opening 48.

Referring now to FIGS. 3-4, an x-ray system 50 incorporating the present invention is shown. The x-ray system 50 includes an oil pump 52, an anode end 54, and a cathode end 56. A central enclosure 58 is provided and positioned between the anode end 54 and the cathode end 56. Housed within the central enclosure 58 is an x-ray generating device or x-ray tube 60. A fluid chamber 62 is provided and housed within a lead lined casing 64. Fluid chamber 62 is typically filled with coolant 66 that will be used to dissipate heat within the x-ray generating device 60. Coolant 66 is typically a dielectric oil, but other coolants including air may be implemented. Oil pump 52 circulates the coolant through the x-ray system 50 to cool the x-ray generating device 60 and to insulate casing 64 from high electrical charges found within vacuum vessel 68. To cool the coolant to proper temperatures, a radiator 70 is provided and positioned at one side of the central enclosure 58. Additionally, fans 72, 74 may be mounted near the radiator 70 to provide cooling air flow over the radiator 70 as the dielectric oil circulates therethrough. Electrical connections are provided in anode receptacle 76 and cathode receptacle 78 that allow electrons 79 to flow through the x-ray system 50.

Casing 64 is typically formed of an aluminum-based material and lined with lead to prevent stray x-ray emissions. A stator 80 is also provided adjacent to vacuum vessel 68 and within the casing 64. A window 82 is provided that allows for x-ray emissions created within the system 50 to exit the system and be projected toward an object, such as, a medical patient for diagnostic imaging. Typically, window 82 is formed in casing 64. Casing 64 is designed such that most generated x-rays 84 are blocked from emission except through window 82. X-ray system 50 includes a pre-subject filter assembly 86 designed to control an attenuation profile of x-rays 84.

Figure 5:
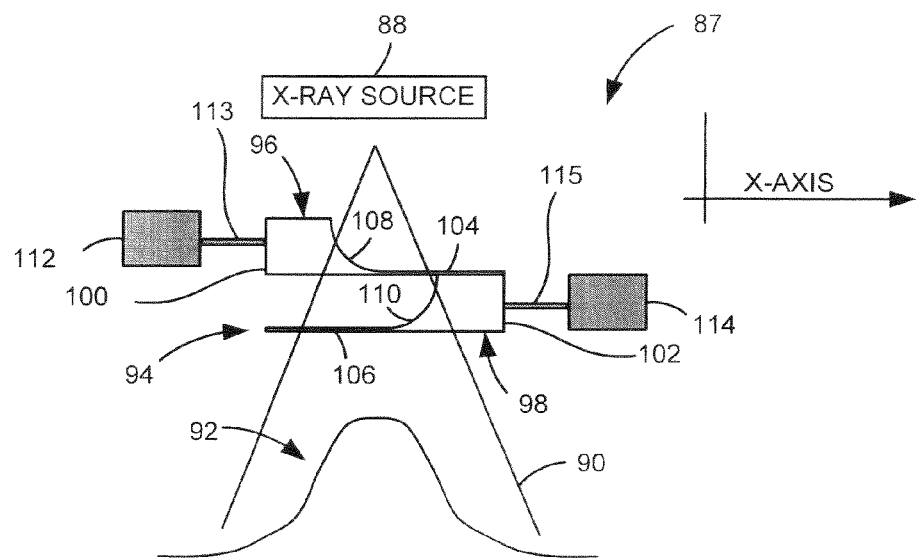
FIG. 5 is a schematic view of one embodiment of a pre-subject, beam shaping filter assembly in accordance with the present invention.

Referring now to FIG. 5, an x-ray generation and filtering assembly in accordance with the present invention and at least applicable with the CT and X-ray systems described above is schematically shown. Assembly 87 includes an x-ray source 88 that projects a beam of x-rays 90, or other high frequency electromagnetic energy beam toward a subject (not shown). As will be described, beam 90 has a profile 92 that is tailored to at least approximate physical characteristics, e.g. shape, of the subject. Attenuating the x-ray beam 90 prior to attenuation by the subject to define profile 92 is a pre-subject, beam-shaping filter assembly 94.

Filter assembly 94 includes a pair of filters or filter components 96 and 98 that generally mirror each other in shape and orientation. In this regard, each filter 96,98 constitutes roughly one-half of the filter assembly. As will be described below, in a preferred embodiment, the filters are not dimensionally equivalent. Notwithstanding the differences in sizes, each filter is defined by a base 100, 102, a tail 104, 106, and a curved or arcuate portion 108, 110. In this regard, attenuation of x-rays by each filter is non-uniform across the filter body. That is, since the base of each filter is thicker than the tail of each filter, the bases of each filter attenuate more x-rays than the tails of each filter. In one embodiment, the base of each filter has a thickness of 30 mm and each tail has a thickness of 0.25 mm. The degree of attenuation is function of the attenuation material used to fabricate the filter and the relative thickness of each filter portion.

Each filter 96, 98 is operationally connected to a motor assembly 112, 114, respectively. Each motor assembly receives control signals from a controller and/or computer of the imaging system, that when received, causes each motor assembly to position a respective filter in the x-ray beam or path 90. In one embodiment, each motor assembly includes a stepper motor, but it is contemplated that other types of motors may be used to position the filters. The motor assemblies 112, 114 are also designed to re-position the filters independently throughout data acquisition. In this regard, each filter may be separately and dynamically controlled or positioned to achieve a particular attenuation profile 92 throughout data acquisition. Moreover, it is preferred that both filters are connected and controlled by a respective motor assembly. Additionally, one filter could be fixed and remain stationary to the other filter. It is further contemplated that more than two filters may be used.

In an exemplary embodiment, the distal end (relative to the x-ray source) of filter 96 is 117 mm from the x-ray source 88. The distal end of filter 98 is set at 148 mm from the x-ray source in this exemplary embodiment. Additionally, in this exemplary embodiment, the base of filter 96 has a length along the x-axis of 45 mm, the tail has a length of 135 mm, and the connecting curved portion has a length of 24.9 mm. In contrast, the base of filter 98 has a length in the x-direction of 53 mm, the tail has a length of 168 mm, and the connected curved portion has a length of 34.2 mm. The dimensions of each curved portion are set forth in the table below. One skilled in the art will readily appreciate that the above dimensions are illustrative of only one of a number of possible embodiments.

CURVATURE X, Y COORDINATE DIMENSIONS

| Filter 96 X | Filter 96 Y | Filter 98 X | Filter 98 Y |
|---|---|---|---|
| 0.00000 | 0.140964 | 0.00000 | 0.140964 |
| 1.52658 | 0.277455 | 1.92109 | 0.277455 |
| 3.02431 | 0.736801 | 3.81409 | 0.736801 |
| 4.48315 | 1.49686 | 5.66911 | 1.49686 |
| 5.89467 | 2.53118 | 7.47786 | 2.53118 |
| 7.25198 | 3.81159 | 9.23358 | 3.81159 |
| 8.54973 | 5.30908 | 10.9311 | 5.30908 |
| 9.78406 | 6.99454 | 12.5666 | 6.99454 |
| 10.9524 | 8.83954 | 14.1378 | 8.83954 |
| 12.0536 | 10.8169 | 15.6436 | 10.8169 |
| 13.0874 | 12.9009 | 17.0839 | 12.9009 |
| 14.0545 | 15.0681 | 18.4596 | 15.0681 |
| 14.9562 | 17.2971 | 19.7722 | 17.2971 |
| 15.7946 | 19.5688 | 21.0238 | 19.5688 |
| 16.5720 | 21.8668 | 22.2169 | 21.8668 |
| 17.2910 | 24.1766 | 23.3544 | 24.1766 |
| 17.9543 | 26.4862 | 24.4391 | 26.4862 |
| 18.8075 | 27.9529 | 25.7168 | 27.9529 |
| 19.8335 | 28.7495 | 27.1705 | 28.7495 |
| 20.9281 | 29.2923 | 28.6963 | 29.2923 |
| 22.0739 | 29.6668 | 30.2769 | 29.6668 |
| 23.2688 | 29.9013 | 31.9104 | 29.9013 |
| 24.5186 | 29.9983 | 33.6029 | 29.9983 |

Motor assemblies 112, 114 axially and independently position filters 96, 98, respectively, along the x-direction in the x-ray path so that the collective attenuation of the filters defines a target attenuation profile. In one embodiment, each motor positions a respective filter by extending and retracting respective piston assemblies 113 and 115. One skilled in the art will appreciate that other assemblies may be used to extend and retract the filters into and from the x-ray path. Based on the positioning of the filters, the attenuation caused by filter 96 is added to the attenuation caused by filter 98. Since each filter has a contour that defines a multiple thickness, the combined contours collectively define a multitude of possible beam profiles. A particular beam profile may therefore be selected from the multitude of possible beam profiles so that that the resulting beam profile is tailored to the particular patient or subject. That is, filters 96, 98 may be positioned relative to one another by their respective motor assemblies 112, 114 to define a beam profile that substantially matches an approximate shape of the patient. Also, filters 96 and 98 are shown as at least partially overlapping one another. It is contemplated, however, that the filters be positioned such that no overlapping occurs.

Figure 6:
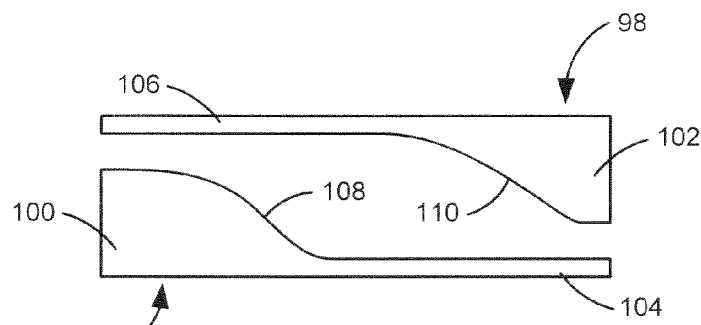
FIG. 6 is a schematic view of another embodiment of a pre-subject, beam shaping filter in accordance with the present invention.

Shown in FIG. 6 is another embodiment of the present invention. To reduce size constraints on the CT or x-ray system, filters 96 and 98, as shown in FIG. 6, are oriented with respect to one another such that the tail 104 of filter 96 is positioned proximate to the base 102 of filter 98. Similar to the orientation of FIG. 5, a desired attenuation profile may be formed by independently positioning filters 96 and 98 relative to one another. Additionally, the volume occupied by the orientation shown in FIG. 6 is effectively one-half of that required by the orientation of FIG. 5. It should be noted that in the orientation shown in FIG. 6, it is preferred that filter 98 have a shape different from that of filter 96 so that the x-ray path lengths are identical for both filters. Determining the appropriate shape may be achieved by determining the path length for each fan angle on filter 96 and then locating (determining) the location of the filter boundary on filter 98 with the same fan angle.

Figure 7:
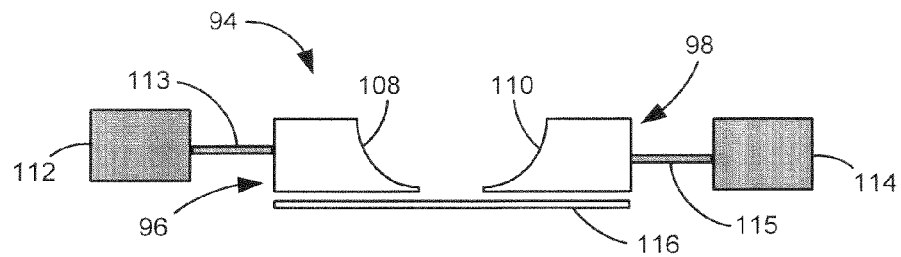
FIG. 7 is a schematic view of another embodiment of a filter assembly in accordance with the present invention.

Referring now to FIG. 7, another embodiment of a filter assembly in accordance with the present invention is schematically shown. In this embodiment, filters 96 and 98 are constructed without tail portions 104 and 106, respectively. In this regard, each filter 96 and 98 have a base 100, 102 and a curved portion 108, 110. Replacing the tail portions is a retractable or stationary, and relatively thin attenuation plate 116. In the illustrated embodiment, plate 116 is fixed, but it is contemplated that plate 116 may be connected to a motor assembly that controls the position of plate 116 in the x-ray path. Plate 116 also operates to provide a minimum, non-zero amount of attenuation if filters 96 and 98 are separated from one another, i.e. no filter overlap.

As described, filters 96 and 98 may be positioned in the x-ray path by respective motor assemblies. The positioning of the filters 96 and 98 may be set prior to the beginning of a scan and remained fixed during data acquisition, or filters 96 and 98 may be dynamically and automatically re-positioned throughout the data acquisition process to achieve a desired or target attenuation profile. In either case, it is preferred to carry out a scout scan of the subject to determine an optimal beam profile for that particular subject. The scout scan preferably gathers information relative to the subject's shape and size. One skilled in the art will readily appreciate that other characteristics may be taken into consideration when determining an appropriate attenuation profile. From this scout scan, a computer in the imaging system provides control signals to the respective motor assemblies, that when executed, causes the motor assemblies to position the filters relative to one another in a specified position and, if applicable, to re-position the filters during data acquisition. In this regard, the intensity of the x-ray beam on particular anatomical locations may be precisely controlled.

Referring now to FIG. 8, package/baggage inspection system 118 includes a rotatable gantry 120 having an opening 122 therein through which packages or pieces of baggage may pass. The rotatable gantry 120 houses a high frequency electromagnetic energy source 124 as well as a detector assembly 126. A conveyor system 128 is also provided and includes a conveyor belt 130 supported by structure 132 to automatically and continuously pass packages or baggage pieces 134 through opening 122 to be scanned. Objects 134 are fed through opening 122 by conveyor belt 130, imaging data is then acquired, and the conveyor belt 130 removes the packages 134 from opening 122 in a controlled and continuous manner. As a result, postal inspectors, baggage handlers, and other security personnel may non-invasively inspect the contents of packages 134 for explosives, knives, guns, contraband, etc.

The present invention is directed to a filter assembly for a radiographic imaging scanner that allows the x-ray beam profile to be adjusted along a continuum matched to the particulars of the subject to control a dynamic range of x-ray flux and achieve optimum dose efficiency. Further, the x-ray beam may be controlled during data acquisition to account for an off-centered subject. Moreover, image artifacts are reduced because the filters are absent discontinuous edges or mechanical interfaces. Additionally, manufacturability of the filters is not unduly complex and implementation of the filters does not require extensive changes in existing radiographic imaging system design.

Therefore, in accordance with one embodiment of the present invention, a beam shaping filter assembly is provided. The filter assembly includes a first moveable filter having a non-uniform thickness and a second moveable filter independent of the first moveable filter and having a non-uniform thickness. Each filter is configured to be placed in a high frequency electromagnetic energy beam for attenuation of the beam for radiographic data acquisition.

In accordance with another embodiment, a CT system is disclosed that includes a rotatable gantry having an opening to receive a subject to be scanned and a high frequency electromagnetic energy projection source configured to project a high frequency electromagnetic energy beam toward the subject. A pre-subject filter assembly including a pair of filters and a scintillator array having a plurality of scintillator cells wherein each cell is configured to detect high frequency electromagnetic energy passing through the subject are also provided. The CT system also includes a photodiode array optically coupled to the scintillator array and comprising a plurality of photodiodes configured to detect light output from a corresponding scintillator cell and a data acquisition system (DAS) connected to the photodiode array and configured to receive the photodiode outputs. An image reconstructor is provided and connected to the DAS and configured to reconstruct an image of the subject from the photodiode outputs received by the DAS. The CT system further includes a controller configured to independently position each filter of the pair of filters in the high frequency electromagnetic energy beam so as to modulate the beam to have a profile that substantially matches at least an approximate shape of the subject.

According to another embodiment, the present invention includes an x-ray filter assembly having a first filter and a second filter. A first motor assembly is connected to the first filter and a second motor assembly is connected to the second filter. The first and the second motor assemblies are configured to independently position a respective filter in an x-ray path to define an attenuation profile that substantially approximates a target shape.

The present invention has been described in terms of the preferred embodiment, and it is recognized that equivalents, alternatives, and modifications, aside from those expressly stated, are possible and within the scope of the appending claims.

What is claimed is:

1. An x-ray filter assembly comprising:
   a moveable first filter having a curved portion and a moveable second filter having a curved portion, the moveable first filter and the moveable second filter arranged to move with respect to one another so as to allow formation of a gap therebetween, and wherein the moveable first filter and the moveable second filter mirror one another relative to a central axis of x-ray projection from an x-ray source toward a subject;
   a third filter having a length perpendicular to the central axis of x-ray projection from the x-ray source toward the subject, the length being longer than at least one of the moveable first and the moveable second filters perpendicular to the central axis of x-ray projection and the third filter being positioned more proximate to the subject than either one of the moveable first filter or the moveable second filter, and positioned to allow attenuation of x-rays that pass through the gap between the moveable first filter and the moveable second filter;
   a first motor assembly connected to the moveable first filter and a second motor assembly connected to the moveable second filter; and
   wherein the first and the second motor assemblies are configured to independently position a respective filter in an x-ray path to define an attenuation profile that substantially approximates a target shape.

2. The x-ray filter assembly of claim 1 wherein each moveable filter is defined by a base, the curved portion, and a tail, and wherein the first and the second motor assemblies are further configured to position the moveable first and second filters such that the tail of the moveable first filter is proximate to the tail of the moveable second filter.

3. The x-ray filter assembly of claim 1 wherein the third filter provides a non-zero minimum attenuation when the moveable first and second filters are not overlapping.

4. The x-ray filter assembly of claim 1 wherein the CT system.

5. The x-ray filter assembly of claim 4 wherein the CT system includes a computer programmed to determine the target shape from a scout scan of the subject to be imaged.

6. The x-ray filter assembly of claim 1 wherein the third filter is moveable.

7. A computed tomography (CT) system comprising:
a rotatable gantry having an opening to receive a subject to be scanned in a subject area;
an x-ray projection source configured to project an x-ray beam toward the subject area;
a pre-subject filter assembly including;
a pair of moveable filters, each moveable filter defined by a base, tail, and curved portion connecting the base to the tail, and wherein the pair of moveable filters are arranged such that the curved portion of one moveable filter generally faces an x-ray projection source and the curved portion of the other moveable filter generally faces an x-ray projection source;
a third filter having a length perpendicular to the central axis of x-ray projection from the source toward the subject, the length being longer than at least one filter of the moveable filters perpendicular to the central axis of x-ray projection;
a scintillator array having a plurality of scintillator cells wherein each cell is configured to detect x-rays passing through the subject;
a photodiode array optically coupled to the scintillator array and comprising a plurality of photodiodes configured to detect light output from a corresponding scintillator cell; and
a controller configured to independently position at least one filter of the pair of moveable filters in the x-ray beam so as to modulate the beam to have a profile that substantially matches at least an approximate shape of the subject.

8. The CT system of claim 7 wherein the pair of moveable filters mirror one another relative to the central axis of x-ray projection from the source toward the subject.

9. The CT system of claim 7 wherein the third filter is positioned more proximate to the subject than either one of the moveable filters.

10. The CT system of claim 7 further comprising a computer programmed to cause application of a scout scan of the subject and from the scout scan determine at least an approximate shape of the subject.

11. The CT system of claim 10 wherein the at least one filter of the pair of moveable filters is operationally connected to at least one motor that is operationally connected to the controller such that control signals transmitted to the controller by the computer cause the at least one motor to position the at least one filter of the pair of moveable filters in projection path to modulate the beam to have a desired profile.

12. The CT system of claim 7 wherein the third filter is moveable.

* * * * *

UNITED STATES PATENT AND TRADEMARK OFFICE
CERTIFICATE OF CORRECTION

PATENT NO. : 7,260,182 B2  Page 1 of 1
APPLICATION NO. : 11/419851
DATED : August 21, 2007
INVENTOR(S) : Toth et al.

It is certified that error appears in the above-identified patent and that said Letters Patent is hereby corrected as shown below:

Col. 9, line 4 (Claim 4), delete "wherein the" and substitute therefore -- incorporated into a --;

Col. 9, line 21 (Claim 7), delete "an" and substitute therefore -- the --;

Col. 9, line 23 (Claim 7), delete "an" and substitute therefore -- the --.

Signed and Sealed this

Sixth Day of November, 2007

JON W. DUDAS
*Director of the United States Patent and Trademark Office*